(12) United States Patent
Sutton et al.

(10) Patent No.: US 8,771,161 B2
(45) Date of Patent: Jul. 8, 2014

(54) EXPANDABLE BRACHYTHERAPY APPARATUS AND METHODS FOR USING THEM

(75) Inventors: Doug S. Sutton, Pacifica, CA (US); George D. Hermann, Portola Valley, CA (US)

(73) Assignee: Cianna Medical, Inc., Aliso Viejo, CA (US)

( * ) Notice: Subject to any disclaimer, the term of this patent is extended or adjusted under 35 U.S.C. 154(b) by 532 days.

(21) Appl. No.: 12/642,626

(22) Filed: Dec. 18, 2009

(65) Prior Publication Data
US 2010/0099939 A1 Apr. 22, 2010

Related U.S. Application Data

(62) Division of application No. 11/868,483, filed on Oct. 6, 2007.

(60) Provisional application No. 60/828,655, filed on Oct. 8, 2006.

(51) Int. Cl.
*A61M 36/00* (2006.01)
*A61N 5/10* (2006.01)

(52) U.S. Cl.
CPC ....... *A61N 5/1014* (2013.01); *A61N 2005/1018* (2013.01)
USPC .................................................. 600/7; 600/3

(58) Field of Classification Search
USPC ........ 600/1–8; 604/19–21, 27, 28, 36, 48, 57, 604/93.01, 96.01, 103.03, 506–510
See application file for complete search history.

(56) References Cited

U.S. PATENT DOCUMENTS 3,060,924 A 10/1962 Rush
3,750,653 A 8/1973 Simon
(Continued)

FOREIGN PATENT DOCUMENTS

EP 0318447 5/1989
EP 0390528 1/1997
(Continued)

OTHER PUBLICATIONS

"Cable." Academic Press Dictionary of Science and Technology. Oxford: Elsevier Science & Technology, 1992. Credo Reference. Web. Jun. 17, 2011.*

(Continued)

*Primary Examiner* — Charles A Marmor, II
*Assistant Examiner* — Carrie R Dorna
(74) *Attorney, Agent, or Firm* — William A. English; Vista IP Law Group LLP

(57) ABSTRACT

Apparatus for delivering brachytherapy to a target tissue region includes an elongate body including a proximal end, a distal end sized for introduction into a tissue tract and carrying a plurality of elongate members including pathways for receiving a source of radiation. The elongate members are movable between collapsed and expanded configurations. During use, a tract is created through tissue, and the elongate body carrying the elongate members is advanced through the tract into a target location with the elongate members in the collapsed configuration. The elongate members are directed to the expanded configuration at the target location, and radiation is delivered to treat tissue at the target location, e.g., by introducing one or more radiation sources along the pathways. The apparatus may include features to prevent overexpansion of the elongate members and/or to facilitate rapid collapse of the elongate members.

25 Claims, 9 Drawing Sheets

(56) References Cited

U.S. PATENT DOCUMENTS

| | | | |
|---|---|---|---|
| 3,968,803 A | 7/1976 | Hyman | |
| 4,427,005 A | 1/1984 | Tener | |
| 4,580,561 A | 4/1986 | Williamson | |
| 4,714,074 A | 12/1987 | Rey et al. | |
| 4,798,212 A | 1/1989 | Arana | |
| 4,936,823 A | 6/1990 | Colvin et al. | |
| 4,957,476 A | 9/1990 | Cano | |
| 4,976,680 A | 12/1990 | Hayman et al. | |
| 5,056,523 A | 10/1991 | Hotchkiss, Jr. et al. | |
| 5,106,360 A | 4/1992 | Ishiwara et al. | |
| 5,152,741 A | 10/1992 | Farnio | |
| 5,235,966 A | 8/1993 | Jamner | |
| 5,242,372 A | 9/1993 | Carol | |
| 5,279,565 A | 1/1994 | Klein et al. | |
| 5,302,168 A | 4/1994 | Hess | |
| 5,336,178 A | 8/1994 | Kaplan et al. | |
| 5,354,257 A | 10/1994 | Roubin et al. | |
| 5,411,466 A | 5/1995 | Hess | |
| 5,423,747 A | 6/1995 | Amano | |
| 5,429,605 A | 7/1995 | Richling | |
| 5,484,384 A | 1/1996 | Fearnot | |
| 5,503,613 A | 4/1996 | Weinberger | |
| 5,509,900 A | 4/1996 | Kirkman | |
| 5,538,502 A | 7/1996 | Johnstone | |
| 5,540,659 A | 7/1996 | Teirstein | |
| 5,611,767 A | 3/1997 | Williams | |
| 5,653,683 A | 8/1997 | D'Andrea | |
| 5,678,572 A | 10/1997 | Shaw et al. | |
| 5,707,332 A | 1/1998 | Weinberger | |
| 5,713,828 A | 2/1998 | Coniglione | |
| 5,720,717 A | 2/1998 | D'Andrea | |
| 5,730,698 A | 3/1998 | Fischell et al. | |
| 5,782,740 A | 7/1998 | Schneiderman | |
| 5,840,008 A | 11/1998 | Klein et al. | |
| 5,843,163 A | 12/1998 | Wall | |
| 5,851,171 A | 12/1998 | Gasson | |
| 5,863,284 A | 1/1999 | Klein | |
| 5,882,291 A | 3/1999 | Bradshaw et al. | |
| 5,891,091 A | 4/1999 | Teirstein | |
| 5,910,102 A | 6/1999 | Hastings | |
| 5,913,813 A | 6/1999 | Williams et al. | |
| 5,916,143 A | 6/1999 | Apple et al. | |
| 5,931,774 A | 8/1999 | Williams et al. | |
| 5,938,582 A | 8/1999 | Ciamacco, Jr. et al. | |
| 5,942,209 A | 8/1999 | Leavitt et al. | |
| 5,976,106 A | 11/1999 | Verin et al. | |
| 6,013,019 A * | 1/2000 | Fischell et al. | 600/3 |
| 6,022,308 A | 2/2000 | Williams | |
| 6,033,357 A | 3/2000 | Ciezki et al. | |
| 6,036,632 A | 3/2000 | Whitmore et al. | |
| 6,056,722 A | 5/2000 | Jayaraman | |
| 6,059,752 A | 5/2000 | Segal | |
| 6,071,263 A | 6/2000 | Kirkman | |
| 6,074,339 A | 6/2000 | Gambale et al. | |
| 6,083,148 A | 7/2000 | Williams | |
| 6,099,454 A * | 8/2000 | Hastings et al. | 600/3 |
| 6,117,064 A | 9/2000 | Apple et al. | |
| 6,159,139 A | 12/2000 | Chiu | |
| 6,159,141 A | 12/2000 | Apple et al. | |
| 6,176,821 B1 | 1/2001 | Crocker et al. | |
| 6,179,766 B1 | 1/2001 | Dickerson | |
| 6,196,996 B1 | 3/2001 | Teirstein | |
| 6,200,256 B1 | 3/2001 | Weinberger | |
| 6,200,257 B1 | 3/2001 | Winkler | |
| 6,213,976 B1 | 4/2001 | Trerotola | |
| 6,217,585 B1 | 4/2001 | Houser et al. | |
| 6,221,003 B1 | 4/2001 | Sierocuk et al. | |
| 6,221,030 B1 | 4/2001 | Avaltroni | |
| 6,234,951 B1 | 5/2001 | Hastings | |
| 6,238,374 B1 | 5/2001 | Winkler | |
| 6,258,099 B1 | 7/2001 | Mareiro et al. | |
| 6,261,320 B1 | 7/2001 | Tam et al. | |
| 6,264,599 B1 | 7/2001 | Slater et al. | |
| 6,264,631 B1 | 7/2001 | Willis et al. | |
| 6,267,775 B1 | 7/2001 | Clerc et al. | |
| 6,287,249 B1 | 9/2001 | Tam et al. | |
| 6,338,709 B1 | 1/2002 | Geoffrion | |
| 6,358,195 B1 | 3/2002 | Green et al. | |
| 6,371,904 B1 | 4/2002 | Sirimanne et al. | |
| 6,413,204 B1 | 7/2002 | Winkler et al. | |
| 6,416,457 B1 * | 7/2002 | Urick et al. | 600/3 |
| 6,458,069 B1 | 10/2002 | Tam et al. | |
| 6,482,142 B1 | 11/2002 | Winkler et al. | |
| 6,482,178 B1 | 11/2002 | Andrews et al. | |
| 6,494,824 B1 | 12/2002 | Apple et al. | |
| 6,506,145 B1 | 1/2003 | Bradshaw et al. | |
| 6,508,784 B1 | 1/2003 | Shu | |
| 6,527,692 B1 | 3/2003 | Weinberger | |
| 6,527,693 B2 | 3/2003 | Munro, III et al. | |
| 6,540,656 B2 | 4/2003 | Fontayne et al. | |
| 6,540,734 B1 | 4/2003 | Chiu et al. | |
| 6,554,757 B1 | 4/2003 | Geitz | |
| 6,582,353 B1 | 6/2003 | Hastings et al. | |
| 6,589,158 B2 | 7/2003 | Winkler | |
| 6,592,548 B2 | 7/2003 | Jayaraman | |
| 6,607,476 B1 | 8/2003 | Barnhart | |
| 6,607,478 B2 | 8/2003 | Williams | |
| 6,638,206 B2 | 10/2003 | Green et al. | |
| 6,641,518 B2 | 11/2003 | Wolfson et al. | |
| 6,645,135 B1 | 11/2003 | Bhat | |
| 6,648,811 B2 | 11/2003 | Sierocuk et al. | |
| 6,659,933 B2 | 12/2003 | Asano | |
| 6,673,006 B2 | 1/2004 | Winkler | |
| 6,676,667 B2 | 1/2004 | Mareiro et al. | |
| 6,685,619 B2 | 2/2004 | Halpern et al. | |
| 6,692,460 B1 | 2/2004 | Jayaraman | |
| 6,699,170 B1 | 3/2004 | Crocker et al. | |
| 6,746,465 B2 | 6/2004 | Diederich et al. | |
| 6,752,752 B2 | 6/2004 | Geitz | |
| 6,752,753 B1 | 6/2004 | Hoskins et al. | |
| 6,910,999 B2 | 6/2005 | Chin et al. | |
| 6,923,754 B2 | 8/2005 | Lubock | |
| 6,955,641 B2 | 10/2005 | Lubock | |
| 7,041,047 B2 | 5/2006 | Gellman et al. | |
| 7,056,276 B2 | 6/2006 | Nakano et al. | |
| 7,357,770 B1 | 4/2008 | Cutrer et al. | |
| 2001/0007071 A1 | 7/2001 | Koblish | |
| 2002/0016583 A1 | 2/2002 | Cragg | |
| 2002/0032359 A1 | 3/2002 | Geoffrion et al. | |
| 2002/0165427 A1 | 11/2002 | Yachia et al. | |
| 2003/0092957 A1 | 5/2003 | Scott et al. | |
| 2003/0114878 A1 | 6/2003 | Diederich et al. | |
| 2003/0158515 A1 | 8/2003 | Gonzalez et al. | |
| 2003/0163017 A1 | 8/2003 | Tam et al. | |
| 2003/0236443 A1 | 12/2003 | Cespedes et al. | |
| 2004/0006305 A1 | 1/2004 | Hebert et al. | |
| 2004/0068231 A1 | 4/2004 | Blondeau | |
| 2004/0087828 A1 | 5/2004 | Green et al. | |
| 2004/0116767 A1 | 6/2004 | Lebovic et al. | |
| 2004/0127765 A1 | 7/2004 | Seiler et al. | |
| 2004/0260142 A1 | 12/2004 | Lovoi | |
| 2005/0061533 A1 | 3/2005 | Lovoi et al. | |
| 2005/0075662 A1 | 4/2005 | Pedersen et al. | |
| 2005/0080313 A1 | 4/2005 | Stewart et al. | |
| 2005/0090845 A1 | 4/2005 | Boyd | |
| 2005/0096647 A1 | 5/2005 | Steinke et al. | |
| 2005/0101823 A1 | 5/2005 | Linares et al. | |
| 2005/0101860 A1 | 5/2005 | Patrick et al. | |
| 2005/0124843 A1 | 6/2005 | Singh | |
| 2005/0182286 A1 | 8/2005 | Lubock | |
| 2005/0240074 A1 | 10/2005 | Lubock | |
| 2006/0015166 A1 | 1/2006 | Kindlein et al. | |
| 2006/0020156 A1 | 1/2006 | Shukla | |
| 2006/0094923 A1 | 5/2006 | Mate | |
| 2006/0100475 A1 * | 5/2006 | White et al. | 600/3 |
| 2006/0116546 A1 | 6/2006 | Eng | |
| 2006/0173233 A1 | 8/2006 | Lovoi | |
| 2006/0173235 A1 | 8/2006 | Lim et al. | |
| 2006/0184192 A1 | 8/2006 | Markworth et al. | |
| 2006/0199990 A1 | 9/2006 | Rioux et al. | |
| 2006/0235365 A1 | 10/2006 | Terwilliger et al. | |
| 2006/0258895 A1 | 11/2006 | Maschke | |
| 2007/0106108 A1 | 5/2007 | Hermann et al. | |
| 2007/0167664 A1 | 7/2007 | Hermann et al. | |

(56) References Cited

U.S. PATENT DOCUMENTS

| | | |
|---|---|---|
| 2007/0167667 A1 | 7/2007 | Lubock et al. |
| 2007/0191668 A1 | 8/2007 | Lubock et al. |
| 2008/0091055 A1 | 4/2008 | Nguyen |

FOREIGN PATENT DOCUMENTS

| | | |
|---|---|---|
| EP | 0775505 | 5/1997 |
| EP | 0536888 | 1/1998 |
| EP | 0906769 | 4/1999 |
| EP | 0955071 | 11/1999 |
| EP | 1402922 | 3/2004 |
| EP | 1405600 | 4/2004 |
| EP | 1428477 | 6/2004 |
| EP | 1568397 | 8/2005 |
| WO | 9718012 A | 5/1997 |
| WO | 00/59378 | 10/2000 |
| WO | 01/95808 | 12/2001 |
| WO | 03/077768 | 9/2003 |
| WO | 03/079907 | 10/2003 |

OTHER PUBLICATIONS

European Patent Office, European Search Report on European Patent Application No. EP11170445; EPO Forms 1507N, P0459, 1503, and 1703; Sep. 15, 2011, 6 pages.

* cited by examiner

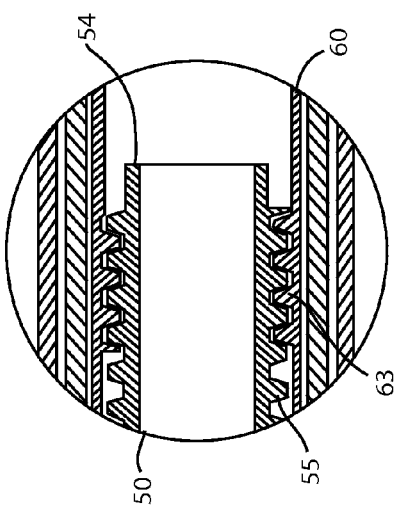
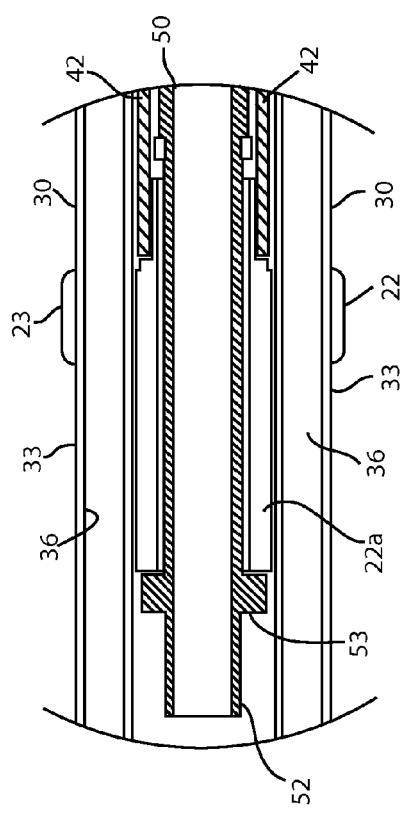
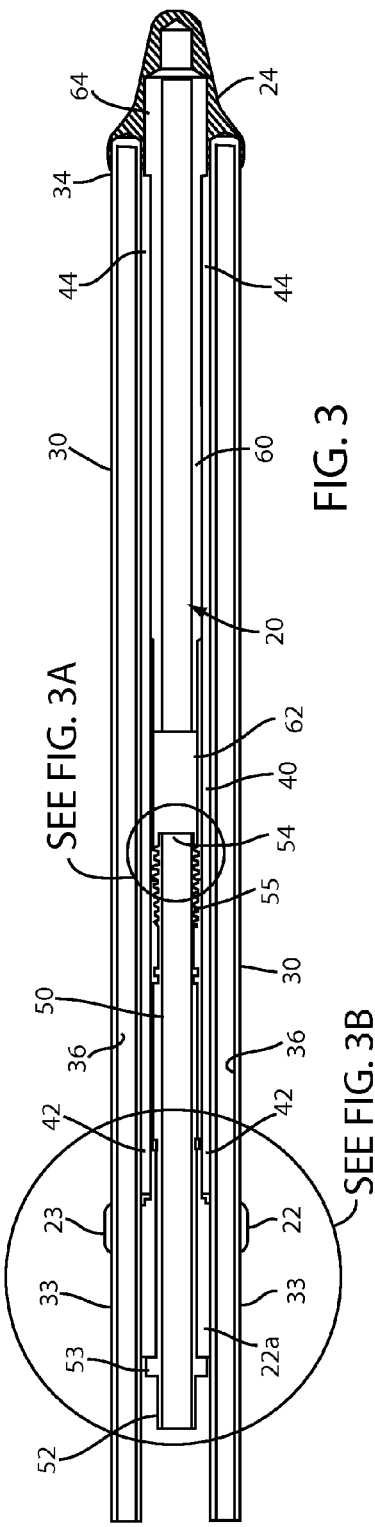

EXPANDABLE BRACHYTHERAPY APPARATUS AND METHODS FOR USING THEM

This application is a divisional of co-pending application Ser. No. 11/868,483, filed Oct. 6, 2007, which claims benefit of provisional application Ser. No. 60/828,655, filed Oct. 8, 2006, the entire disclosure of which is expressly incorporated by reference herein.

FIELD OF THE INVENTION

The present invention relates generally to apparatus, methods, and systems for providing brachytherapy to a human or other mammalian body, and more particularly to expandable apparatus for performing brachytherapy treatment within tissue, e.g., within breast tissue and/or within a body cavity, and to methods for performing brachytherapy using such apparatus.

BACKGROUND

Brachytherapy is a type of radiation therapy used to treat malignant tumors, such as cancer of the breast or prostate. In general, brachytherapy involves positioning a radiation source directly into target tissue, which may include a tumor and/or tissue surrounding a cavity or void, which may contain potentially cancerous cells (such as a cavity or void created by removing a tumor).

Brachytherapy is often divided into two categories: high dose rate (HDR) and low dose rate (LDR) brachytherapy. In HDR brachytherapy, a high activity radiation source is placed into target tissue, often via a previously implanted catheter, for a short period of time, e.g., lasting from several seconds to a few minutes. In contrast, LDR brachytherapy places a low activity radiation source into the target tissue for a longer, sometimes indefinite, period of time.

Both forms of brachytherapy have advantages. For instance, HDR brachytherapy provides higher radiation levels delivered over a shorter dose delivery period. LDR brachytherapy, on the other hand, utilizes lower activity radiation sources. The energy field of the LDR radiation source results in a measured and localized dose of radiation delivered to target tissue, e.g., a tumor, gland, or other tissue surrounding a cavity or void. However, the energy field thereafter decays to avoid excessive exposure of nearby healthy tissue.

Due in part to the lower activity of LDR radiation sources, LDR brachytherapy may provide various advantages. For example, for healthcare workers, exposure precautions for LDR brachytherapy may be less stringent than those for HDR brachytherapy. Also, there are radiobiological advantages of LDR brachytherapy over HDR brachytherapy (e.g., the dose rate effect), which may lead to better sparing of normal tissue during treatment. Moreover, for patients, the relatively longer implantation period associated with LDR brachytherapy may result in fewer visits to a healthcare facility over the course of radiation treatment, as compared to HDR brachytherapy where patients must return to the healthcare facility for each fraction of radiation delivered, which, for breast brachytherapy, may typically include eight to ten (8-10) fractions.

Common radiation sources used in LDR brachytherapy include radioactive isotopes such as Palladium (Pd)-103, Iodine (I)-125, Gold (Au)-198, and Iridium (Ir)-192. While the size and shape of the isotopes may vary, they may be provided in a standardized size of cylindrically shaped capsules that are approximately the size of a grain of rice, e.g., about 0.8 millimeter in diameter and about 4.5 millimeters in length, and are often referred to as "seeds."

LDR seeds are often delivered through needles using a guide template. The guide template may include a matrix of holes that guide the longitudinal advancement of the needles to ensure their proper position relative to the target tissue. Once the needles are properly located in the target tissue, the seeds may be deposited along the longitudinal axis of each needle, after which the needles may be withdrawn.

Current brachytherapy implementations have potential drawbacks. For example, LDR seeds are typically left indwelling and free floating within the target tissue and are, therefore, susceptible to migration. Moreover, once implanted, LDR seeds are generally not considered removable or repositionable. LDR brachytherapy may also require careful dose distribution calculations and seed mapping before, and often during, seed implantation. Such calculation and mapping may allow effective radiation delivery to the target tissue volume, while minimizing radiation to surrounding healthy tissue (e.g., the urethra and rectum, for example, in prostate brachytherapy). Yet, while such dose calculation and seed mapping techniques are effective, problems may exist, such as potentially significant variability in accuracy of seed placement among different clinicians.

Yet another issue with conventional LDR brachytherapy techniques is that they may require the radioactive seeds to be manipulated individually at the time of implantation, which may be a time-consuming process. Moreover, conventional LDR delivery needles are generally limited to delivering the seeds linearly (along a relatively straight line). Thus, to achieve a desired therapy profile, numerous implants (e.g., including about 50-100 seeds, as are common with prostate brachytherapy) are often required, in conjunction with potentially complex dose distribution and mapping techniques and equipment.

SUMMARY

The present invention is generally directed to apparatus, systems, and methods for delivering brachytherapy to a localized target tissue region. While the apparatus, systems, and methods described herein may be useful in treating most any area of the body, an exemplary application is treating breast tissue, e.g., breast tumors or lumpectomy cavities. For example, the apparatus, systems, and methods may be used to place and remove a localized radiation source for both neoadjuvant and post-excisional treatment.

In accordance with one embodiment, a brachytherapy treatment apparatus is provided that includes an elongate body including a proximal end and a distal end sized for introduction into a tract through tissue. A plurality of elongate members may be provided on the distal end including pathways for receiving a source of radiation therealong, the elongate members being movable from a collapsed configuration for introduction through a tissue tract to a target location, and an expanded configuration. A source of radiation may be introduceable along the pathways for delivering radiation to the target location.

In accordance with another embodiment, a brachytherapy treatment apparatus is provided that includes an elongate core member including a proximal end and a distal end configured for introduction into a tract through tissue; a distal hub coupled to the distal end of the core member; a proximal hub on the proximal end of the core member and movable axially relative to the distal hub; and a plurality of elongate members coupled to the proximal and distal hubs and extending between the proximal and distal ends of the core member, the elongate members movable from a collapsed configuration for introduction through a tissue tract to a target location, and an expanded configuration when the proximal hub is directed distally relative to the distal hub, the elongate members comprising pathways for receiving a source of radiation thereal- ong.

In one embodiment, the core member may include first and second telescoping tubes, the first tube coupled to the proximal hub and the second tube coupled to the distal hub such that rotation of the first tube relative to the second tube causes the proximal hub to move distally to direct the elongate members towards the expanded configuration.

In another embodiment, the core member may include features that limit distal movement of the proximal hub, e.g., to prevent overexpansion of the elongate members in the expanded configuration. For example, the core member may include first and second telescoping tubes, the first tube coupled to the proximal hub and the second tube coupled to the distal hub such that rotation of the first tube relative to the second tube causes the proximal hub to move distally to direct the elongate members towards the expanded configuration, and the first and second tubes may be telescopingly coupled by mating threads. The threads may be disengaged when the first tube is rotated sufficiently to direct the elongate members to the expanded configuration, thereby limiting further distal movement of the proximal hub.

In yet another embodiment, the apparatus may include a release mechanism, e.g., on the core member and/or the proximal hub, for disengaging the proximal hub from the core member tube to allow rapid collapse of the elongate members from the expanded configuration.

In accordance with still another embodiment, a brachytherapy treatment apparatus is provided that includes an elongate body including a proximal end and a distal end configured for introduction into a tract through tissue; a plurality of elongate members on the distal end including pathways for receiving a source of radiation therealong, the elongate members being movable from a collapsed configuration for introduction through a tissue tract to a target location, and an expanded configuration; and a plurality of marker devices removably receivable along the pathways of respective elongate members.

In accordance with yet another embodiment, a method is provided for brachytherapy treatment of tissue within a body that includes creating a tract through tissue to a target location including a cavity, and advancing an elongate body carrying a plurality of elongate members through the tract into the target location with the elongate members in a collapsed configuration. The elongate members may be directed to an expanded configuration at the target location to position the elongate members away from a central axis such that tissue in the target region (e.g., surrounding the cavity) extends between at least a portion of adjacent elongate members, and radiation may be delivered to the target location to treat tissue at the target location.

In accordance with still another embodiment, a method for brachytherapy treatment of tissue within a body is provided. A tract may be created through tissue to a target location adjacent to a cavity, and an elongate body carrying a plurality of elongate members may be advanced through the tract into the target location with the elongate members in a collapsed configuration. The elongate members may be directed to an expanded configuration at the target location to position the elongate members away from a central axis, and marker devices may be inserted into the elongate members, e.g., before or after being expanded. The apparatus may be imaged, e.g., using CT or ultrasound, the marker devices enhancing imaging of the elongate members in the expanded configuration relative to the target location. A dose plan may be developed based at least on part on the enhanced imaging of the elongate members, and the marker devices may be removed from the elongate members. Radiation may be delivered to the target location to treat tissue at the target location according to the dose plan.

The above summary is not intended to describe each embodiment or every implementation of the present invention. Rather, a more complete understanding of the invention will become apparent and appreciated by reference to the following detailed description and claims in view of the accompanying drawings.

BRIEF DESCRIPTION OF THE DRAWINGS

FIG. 3 is a longitudinal cross-section of a distal portion of the apparatus of FIG. 1A in the collapsed configuration.

FIGS. 3A and 3B are details of the apparatus of FIG. 3.

DETAILED DESCRIPTION OF EXEMPLARY EMBODIMENTS

Figure 1:
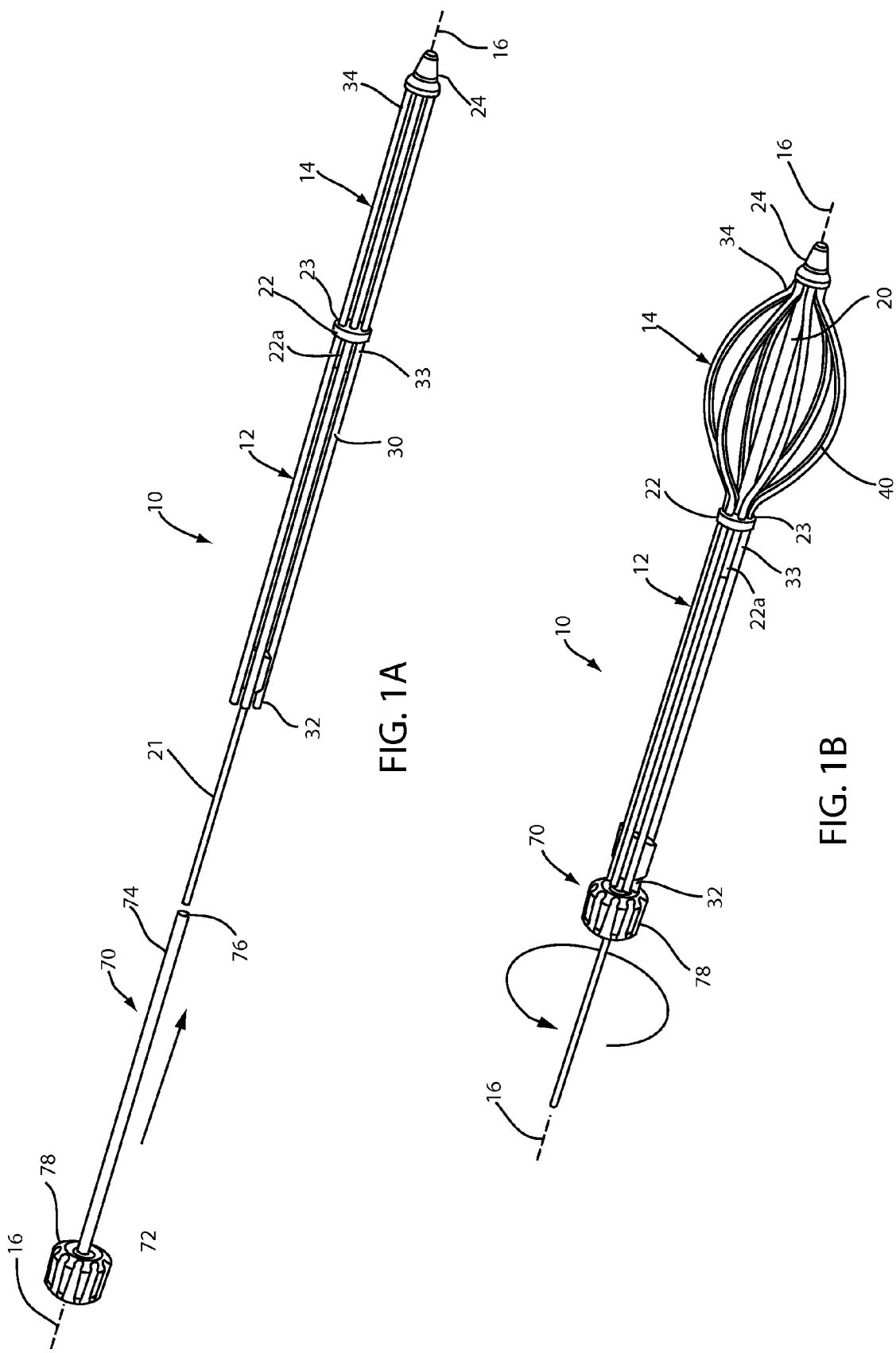
FIG. 1A is a perspective view of an exemplary embodiment of an expandable brachytherapy apparatus in a collapsed or delivery configuration.
FIG. 1B is a perspective view of the apparatus of FIG. 1A in an expanded or deployed configuration.

Generally speaking, the present invention is directed to brachytherapy apparatus, systems, and methods. For example, in one embodiment, a system is provided for delivering one or more therapeutic elements (e.g., radiation sources) relative to a target tissue region. Once delivered, the radiation sources may be either immediately withdrawn (e.g., in HDR applications), or left in place, e.g., implanted, for a defined period of time (e.g., in LDR applications). In either instance, the radiation sources may deliver therapy to the target tissue region in accordance with a predefined therapy profile.

In some embodiments, LDR radiation sources may be implanted and secured to the body or target tissue in such a way as to prevent or substantially limit movement of the sources relative to the target tissue. For example, the apparatus and methods described herein may facilitate indwelling therapy using pre-arranged packages of radioactive sources, e.g., seeds, but also allow easy removal of the radiation sources upon completing brachytherapy treatment.

As used herein, "radiation source" and "radioactive source" may include any therapeutic element operable to deliver a dose of radiation. For example, the radiation source may be one or more radioactive seeds or, alternatively, one or more LDR or HDR wire elements (e.g., Iridium wire), e.g., as disclosed in application Ser. No. 10/658,518, filed Sep. 9, 2003, and published as US 2004/0116767; Ser. No. 11/554,731, filed Oct. 31, 2006, and published as US 2007/167664; Ser. No. 11/276,851, filed Mar. 16, 2006, and published as US 2007/0106108; Ser. No. 11/557,747, filed Nov. 8, 2006, and published as US 2007/167665, and Ser. No. 11/757,231, filed Jun. 1, 2007. The entire disclosures of these applications are expressly incorporated by reference herein.

The term "implantable," as used herein, indicates the capability of a device to be inserted into the body and then maintained in a relatively fixed or static position within the surrounding tissue for an extended period of time, e.g., an hour or more and/or several hours or more, including several days or more.

Furthermore, "target tissue," "target tissue region," "target region," and "target tissue volume," as used herein, may include any portion of a human (or other mammalian) body that has been identified to benefit from radiation therapy. For example, the target tissue region may be a tumor or lesion itself, tissue proximate or surrounding the tumor, or a cavity region created by tumor excision (such as the surrounding tissue or cavity associated with a lumpectomy cavity of the breast).

It should be noted that the apparatus, systems, and methods described herein may be used for LDR or HDR brachytherapy, as described elsewhere herein and in the applications incorporated by reference above. Moreover, while described herein with respect to brachytherapy, the apparatus, systems, and methods may apply to other therapy regimens that benefit from the removable implantation of therapy-delivering elements. In an exemplary application, the apparatus, systems, and methods are described herein for treating breast cancer. However, it will be appreciated that the apparatus, systems, and methods described herein may be used for treating other cancers or conditions that may benefit from brachytherapy treatment.

Figure 4A:
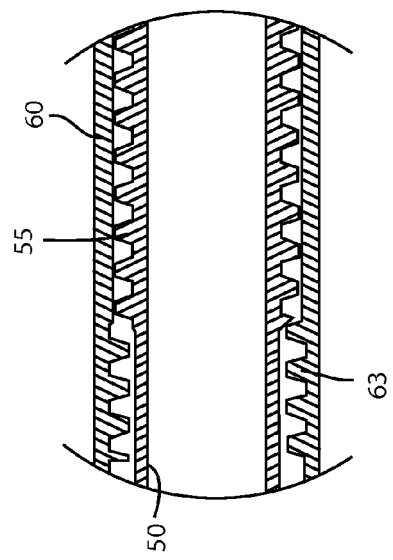
FIGS. 4A and 4B are details of the apparatus of FIG. 4.
Figure 4B:
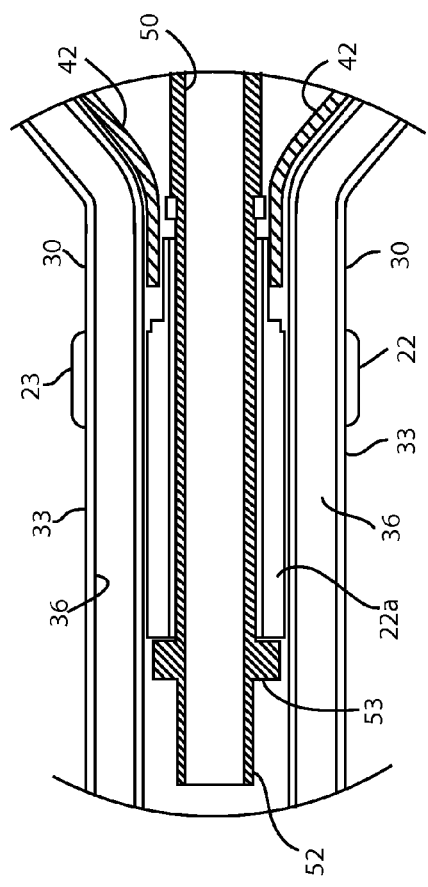
Figure 4:
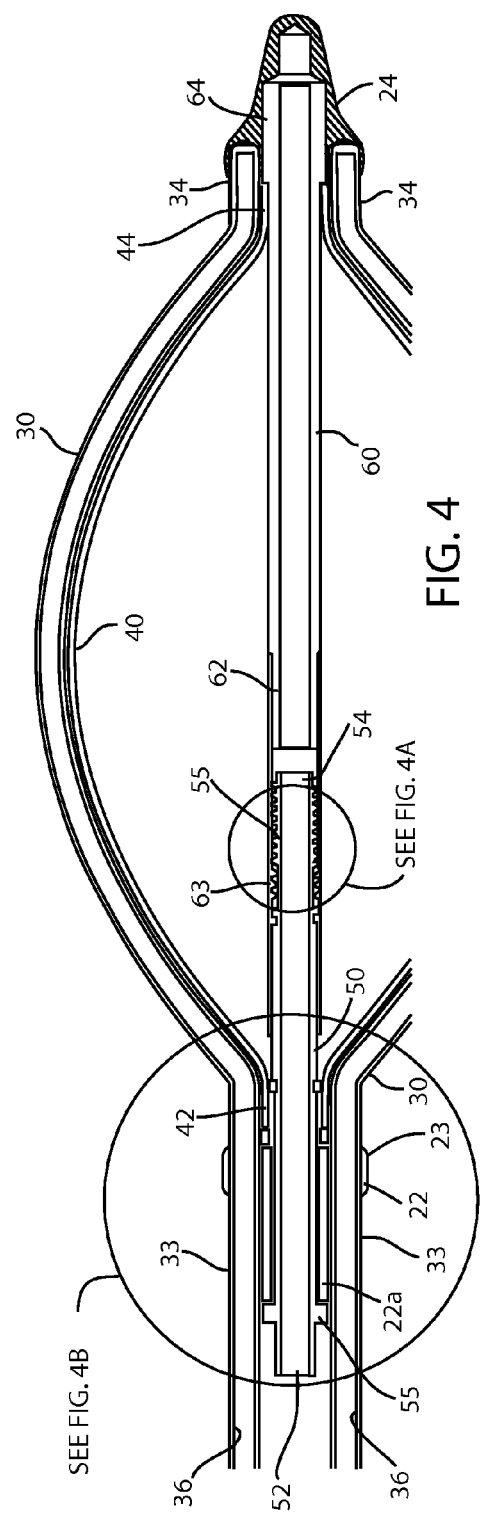
FIG. 4 is a longitudinal cross-section of the distal portion of the apparatus of FIGS. 1B and 2 in the expanded configuration.

Turning to FIGS. 1-5, an exemplary embodiment of an expandable brachytherapy apparatus 10 is shown that generally includes a proximal or tail portion 12, and a distal or therapy delivery portion 14, generally defining a longitudinal axis 16 extending therebetween. As described elsewhere herein, the distal portion 14 may be deployed within a target location of a patient's body, e.g., tumor or cavity within a breast or other body structure (not shown), and the proximal portion 12 may extend from the distal portion 14, e.g., such that the proximal portion 12 protrudes outside of the body structure. The distal portion 14 may be movable between a collapsed configuration, as shown in FIGS. 1A and 3, e.g., for introduction through a tissue tract to a target location, and a fully deployed or expanded configuration, as shown in FIGS. 1B and 4, e.g., for providing a three dimensional array of pathways at the target location, as described further below.

In addition, as shown in FIGS. 1A and 1B, the apparatus 10 may include an expansion tool 70, which may be coupled to the proximal portion 12 of the apparatus 10 for expanding and/or collapsing the distal portion 14, as described further below. The expansion tool 70 may be detachable from the apparatus 10, as shown in FIGS. 1A and 1B, or may be permanently attached to the apparatus 10 (not shown).

Optionally, the apparatus 10 may include one or more other components, e.g., a sheath or other cover (not shown), which may overly the therapy delivery portion 14, e.g., until deployment. In addition or alternatively, a tubular delivery device, such as a catheter, cannula, trocar, obturator, and/or needle (also not shown), may be provided for introducing the apparatus 10 into the target location, e.g., as described in the applications incorporated by reference above. Alternatively, the apparatus 10 may include a sharpened distal tip (not shown), e.g., to facilitate advancement directly through tissue, also as disclosed in the applications incorporated by reference above.

Figure 2:
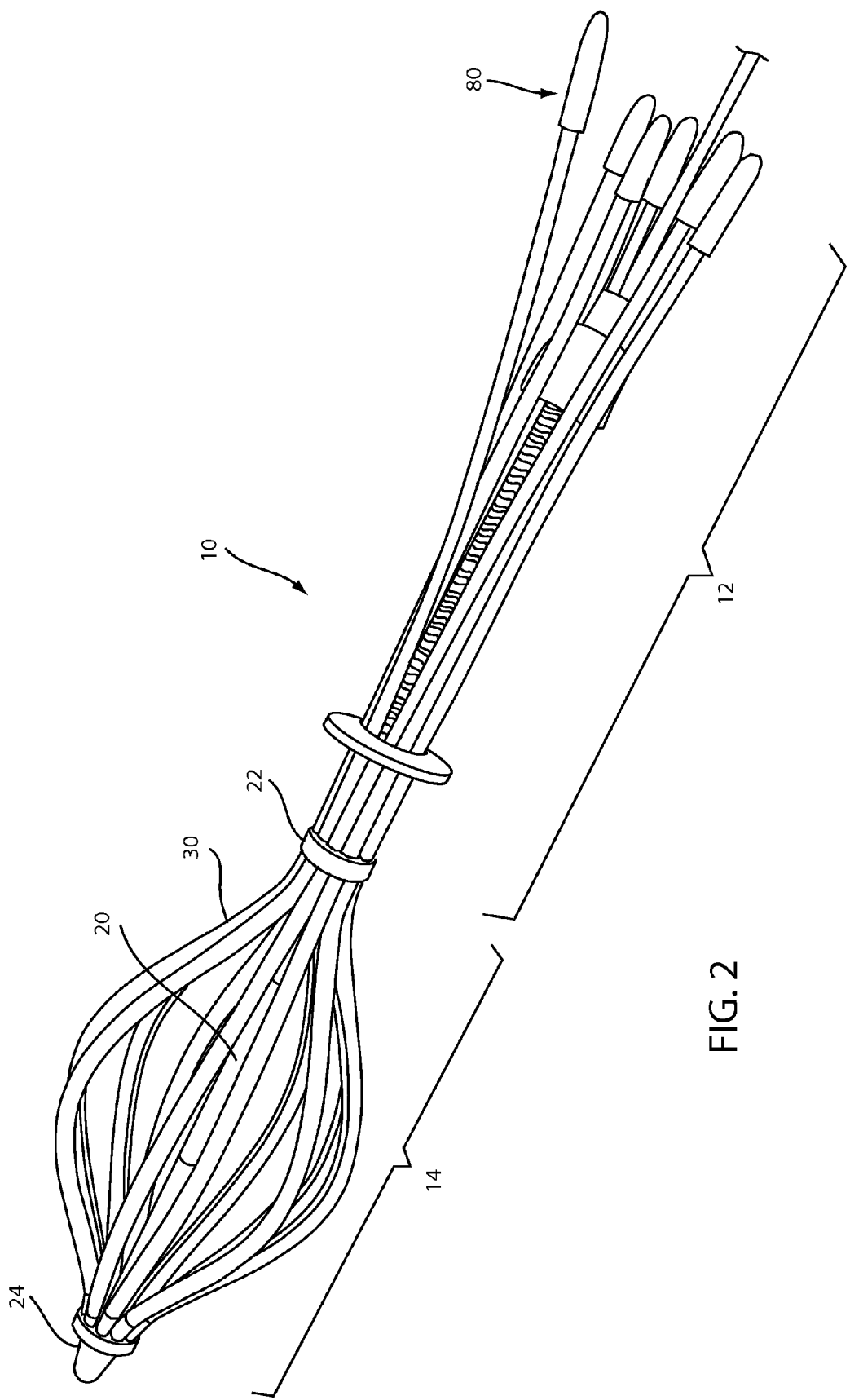
FIG. 2 is another perspective view of the apparatus of FIGS. 1A and 1B in the expanded configuration.

With additional reference to FIG. 2, the apparatus 10 may include an elongate core member 20 extending between a proximal hub 22 and a distal hub 24, and a plurality of flexible elongate members 30 disposed around the core member and/or extending between the proximal and distal hubs 22, 24. The core member 20 may be a substantially rigid member extending between the proximal and distal hubs 22, 24 yet compressible axially to direct the proximal and distal hubs 22, 24 towards and/or away from one another, as described further below.

The elongate members 30 may be elongate tubular members including a proximal end 32, a distal end 34, and a lumen 36 extending therebetween (shown in FIGS. 3 and 4). Each of the proximal ends 32 may include an opening providing access into the respective lumen 36, e.g., for receiving a radiation source, as described elsewhere herein. The proximal ends 32 may remain substantially free relative to one another or may be constrained, e.g., using a collar or other feature, to keep the proximal ends 32 together, organized, and/or otherwise limit movement of the proximal ends 32.

The elongate members 30 may be formed from a single extrusion separated to provide the set of elongate members 30, individual extrusions or other tubular bodies, or may be formed from multiple tubular bodies connected to one another, e.g., by bonding, fusing, lapping, and the like. The elongate members 30 may also include an intermediate portion 33 that is attached to or otherwise secured relative to the proximal hub 22. For example, the intermediate portion 33 may be securely received between an outer collar 23 and an inner main tube hub 22a of the proximal hub 22, e.g., using an interference fit, bonding with adhesive, sonic welding, and the like.

The proximal hub 22 may be provided from a single piece, e.g., such that the outer collar 23 and inner main tube hub 22a are integrally molded or otherwise formed together. Alternatively, the proximal hub 22 may be formed from separate components that are attached together, e.g., using an interference fit, cooperating connectors, bonding using an adhesive, sonic welding, and the like. Optionally, the proximal hub 22 may include individual axial openings for receiving the intermediate portions 33 of respective elongate members 30 therethrough. Alternatively, the elongate members 30 may extend from the distal hub 24 to the proximal hub 22, and terminate within or adjacent the proximal hub 22. In this alternative, separate tubular members (not shown) may be provided that are attached to the elongate members 30 and/or proximal hub 22 to provide the proximal portion 12 of the apparatus 10, while still providing lumens 36 extending from the proximal portion 12 to the distal portion 14.

The distal ends 34 of the elongate members 30 may be received within and/or secured to the distal hub 24. For example, the distal hub 24 may include an annular recess or individual pockets into which the distal ends 34 may be received and secured, e.g., using an interference fit, bonding with an adhesive, sonic welding, and the like. The distal hub 24 may provide a rounded and/or tapered distal tip for the apparatus 10, e.g., to facilitate introduction into a patient's body. Alternatively, the distal hub 24 may include a pointed or other sharpened distal tip (not shown) for facilitating advancing the apparatus 10 directly through tissue (not shown).

Optionally, the distal hub 24 may be formed from radiolucent material, e.g., non-metallic material such as glass-filled nylon combined with isoprene rubber. If the distal hub 24 is formed from radiolucent material, radiopaque markers, such as the marker device 80 shown in FIG. 6 and described elsewhere herein, may be placed inside the lumens 36 of the elongate members 30 to determine the position of the distal ends 34 of the elongate members 30 during dose planning, also as described further elsewhere herein.

Figure 5:
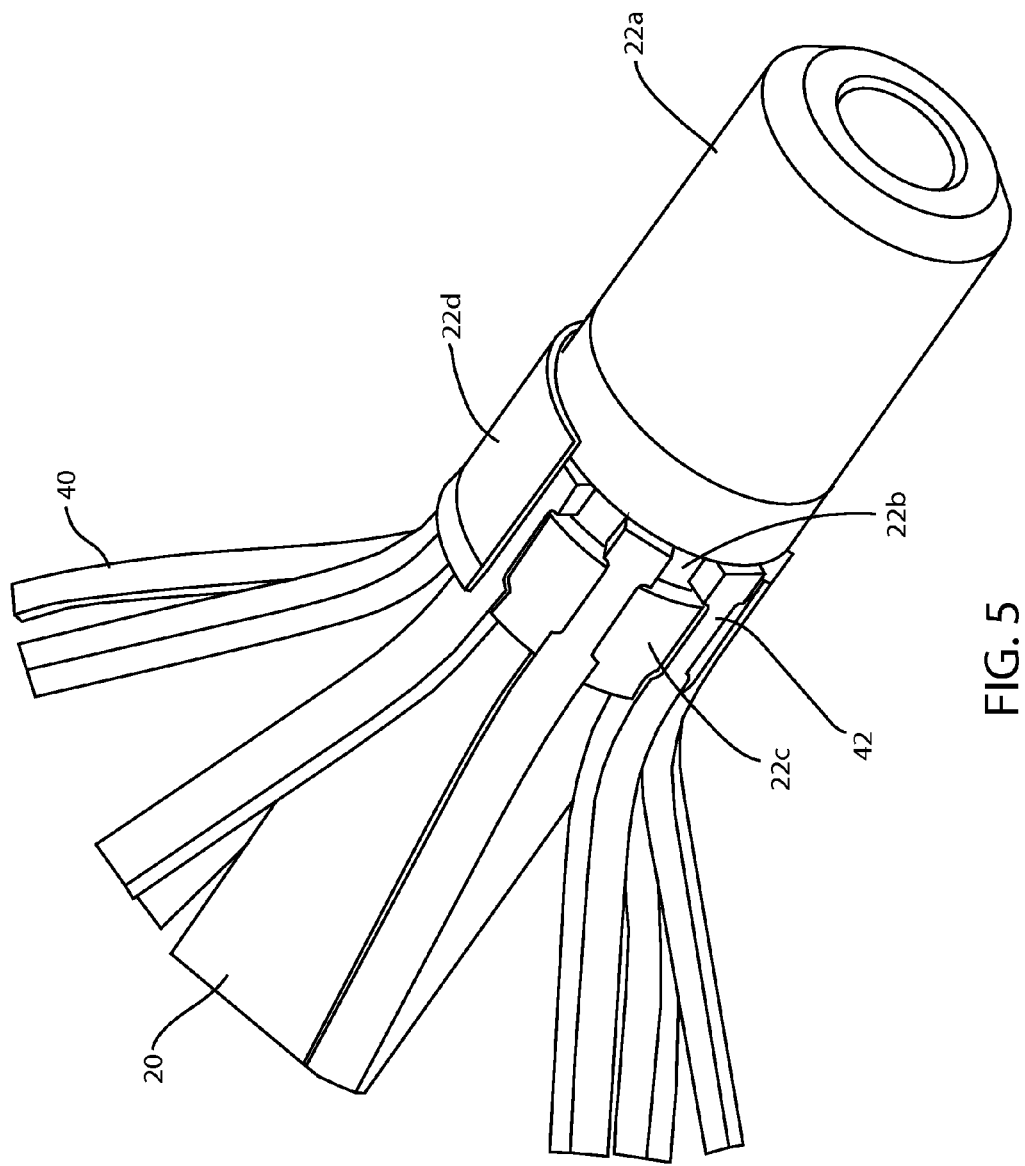
FIG. 5 is a perspective view of a proximal hub of the apparatus of FIGS. 1-4, showing attachment of support members to the proximal hub.

In addition, as shown in FIGS. 3-5, the apparatus 10 may include supports 40 extending along the elongate members 30, e.g., between the intermediate portions 33 and the distal ends 34, i.e., along at least the distal portion 14 of the apparatus 10. In an exemplary embodiment, the supports 40 may be elongate strips of material, e.g., metal, such as stainless steel or Nitinol, plastic, or composite material, that may be elastically deflected during use of the apparatus 10, e.g., when the distal portion 14 is directed between the collapsed and expanded configurations. The supports 40 generally include a proximal end 42 attached or secured to the intermediate portion 33 of the elongate members 30 and/or the proximal hub 22, and a distal end 44 attached or secured to the distal end 34 of the elongate members 30 and/or the distal hub 24. For example, the supports 40 may be disposed along an outer surface of the tubular members 30 along a side closest to the core member 20. The supports 40 may be attached or otherwise secured to the tubular members 30, e.g., using shrink tubing, bonding with an adhesive, sonic welding, and the like.

Alternatively, the supports 40 may be provided within an additional lumen (not shown) within the elongate members 30, similar to embodiments disclosed in the applications incorporated by reference above. In a further alternative, the supports 40 may be eliminated. For example, the elongate members 30 may be configured, e.g., may have asymmetrical cross-sections, to bias the elongate members 30 to expand radially in a predetermined manner, as disclosed in the applications incorporated by reference above. Optionally, the supports 40 may provide shielding, in addition to or instead of supporting the elongate members 30, also as disclosed in the applications incorporated by reference above.

In an exemplary embodiment, as shown in FIG. 5, the proximal ends 42 of the supports 40 may be secured to the proximal hub 22, e.g., to prevent migration of the supports 40. For example, the inner main tube hub 22a may include an annular groove 22b, and a plurality of axial grooves 22c extending distally from the annular groove 22b. The proximal ends 42 of the supports 40 may be received within respective axial grooves 22c and/or into the annular groove 22b. As shown, the proximal ends 42 of the supports 40 include a "dog bone," "I," or "T" shaped feature such that a portion of the dog bone feature is received within the respective axial groove 22c and extends into the annular groove 22b. The dog bone features may mate with the grooves 22b, 22c in the proximal hub 22 to provide structural stability to the apparatus 10 in the fully deployed configuration. For example, the interface may prevent axial movement of the supports 40 while also enhancing lateral stability of the supports 40, and consequently, the elongate members 30. The dog bone features may be force fit into the grooves 22b, 22c and/or may be bonded into the grooves 22b, 22c.

Optionally, a locking ring 22d (shown only partially in FIG. 5 for clarity) may be received around the inner main tube hub 22a and over the proximal ends 42, axial grooves 22c, and/or annular groove 22b to prevent the proximal ends 42 from separating from the proximal hub 22. The locking ring 22d may be received around the inner main tube hub 22a and secured thereto, such as, using an interference fit, heat shrinking (e.g., if the locking ring 22d is formed from heat shrink tubing), bonding using an adhesive, sonic welding, and the like. In addition or alternatively, the proximal ends 22 may be attached to the proximal hub 22 and/or intermediate portions 33 of the elongate members 30, e.g., using an interference fit, bonding with an adhesive, sonic welding, and the like.

The supports 40 may be oriented such that their major dimension is disposed generally circumferentially relative to the core member 20 and their minor dimension is disposed generally radially. In the collapsed configuration, the supports 40 may extend substantially axially, i.e., substantially parallel to the core member 20. As described further below, when the proximal and distal hubs 22, 24 are directed towards one another, the supports 40 may bow radially outwardly between the proximal and distal ends 42, 44, thereby controlling expansion of the elongate members 30 as they are directed towards the expanded configuration.

Turning to FIGS. 3 and 4, the core member 20 may include telescoping elongate members that allow the proximal and distal hubs 22, 24 to be moved axially towards and away from one another. As shown, the core member 20 includes a first or proximal tube 50 including proximal and distal ends 52, 54, and a second or distal tube 60 also including proximal and distal ends 62, 64. The proximal and distal tubes 50, 60 may interact with one another, i.e., at the distal end 54 and the proximal end 62, e.g., to allow the proximal tube 50 to telescope at least partially into the distal tube 60 (or alternatively the distal tube 60 may telescope into the proximal tube 50).

As shown, the distal end 64 of the distal tube 60 is received within the distal hub 24. The distal end 64 may be secured to the distal hub 24, e.g., using an interference fit, cooperating connectors, bonding using an adhesive, sonic welding, and the like. Thus, the distal tube 60 may remain substantially stationary relative to the distal hub 64 and the distal ends 34 of the elongate members 30.

The proximal end 62 of the distal tube 60 includes internal threads 63 extending for a predetermined distance along the length of the proximal end 62. Thus, the proximal end 62 may also include an unthreaded region distal to the internal threads 63. The distal tube 60 may be formed as a single tubular segment extending between the proximal and distal ends 62, 64, thereby defining a lumen 66. Alternatively, the distal tube 60 may be formed from multiple segments attached to one another. For example, the distal tube 60 may include a first tubular segment defining the proximal end 62, e.g., including the internal threads 63 and the unthreaded region, and a second segment extending from the proximal end 62 to the distal end 64. The first and second segments may be attached to one another, e.g., using mating threads or other cooperating connectors, interference fit, bonding using an adhesive, welding, sonic welding, and the like. The second segment may be a tubular or solid rod segment, depending upon whether it is desired to extend the lumen 66 from the proximal end 62 entirely to the distal end 64.

The proximal tube 50 also includes a lumen 56 extending between the proximal and distal ends 52, 54. The lumen 56 may communicate with the lumen 66 in the distal tube 60, e.g., if it is desired to introduce a radiation source or other device through the core member 20 at least partially towards the distal hub 24. The proximal tube 50 may be slidably disposed within or otherwise received through the proximal hub 22, as shown in FIGS. 3 and 4. In particular, the proximal tube 50 may be free to rotate about the longitudinal axis 16 within the proximal hub 22, thereby allowing the proximal tube 50 to rotate and thread into or out of the distal tube 60.

In addition, the proximal tube 50 may include a stop, e.g., an annular rib 53, radial tabs (not shown), and the like on the proximal end 52 disposed proximal and adjacent to the proximal hub 22, as best seen in FIG. 3B. Thus, although the proximal hub 50 is free to rotate within the proximal hub 22, when the proximal tube 50 is rotated to thread the distal end 54 into the proximal end 62 of the distal tube 60, the stop 53 may abut the proximal hub 22. Alternatively, the stop 53 may be received within an annular groove or pocket within the proximal hub 22. This alternative may directly couple axial movement of the proximal hub 22 to the proximal tube 50, e.g., when the proximal tube 50 is rotated to move distally and/or proximally.

With particular reference to FIG. 3, the apparatus 10 may be provided with the proximal tube 50 of the core member 20 in its proximal position, i.e., thereby providing the elongate members 30 in the collapsed condition. As shown, the elongate members 30 and supports 40 may extend substantially axially along the core member 20 in the collapsed condition. As shown in FIG. 3A, the external and internal threads 55, 63 may be engaged with one another such that rotation of the proximal tube 50 in a first direction, e.g., clockwise, causes the threads 55, 63 to direct the proximal tube 50 distally. As shown in FIG. 3B, the stop 53 on the proximal tube 50 may abut or be disposed within the proximal hub 22 until the proximal tube 50 begins threading into the distal tube 60.

Turning to FIG. 4, because of the interaction between the stop 53 and the proximal hub 22, rotation of the proximal tube 50 in the first direction causes the proximal hub 22 to be directed distally towards the distal hub 24, as indicated in FIG. 4B. As the proximal hub 22 is directed towards the distal hub 24, the elongate members 30 between the intermediate portions 33 and the distal ends 34 become subjected to an axially compressive force, which causes the elongate members 30 to bow radially outwardly towards the expanded configuration, as shown in FIG. 4. As described elsewhere herein, the elongate members 30 may expand into a predetermined shape in the expanded configuration, e.g., due to the supports 40 and/or the configuration of the elongate members 30. For example, the elongate members 30 may be directed into a generally spherical shape, an elliptical shape, and the like, including single or multiple layers, as disclosed in the applications incorporated by reference above.

As best seen in FIG. 4A, the proximal tube 50 may be rotated until the external threads 55 pass entirely through the internal threads 63 and into the unthreaded region of the distal tube 60. At this point, further rotation of the proximal tube 50 causes the proximal tube 50 to simply spin freely within the distal tube 60 without causing further distal movement of the proximal hub 22. This freedom of motion may provide tactile feedback to the user that the elongate members 30 have been fully expanded to the expanded configuration. Optionally, when the external threads 55 enter the unthreaded region, the user may hear an audible "click" also providing confirmation that the elongate members 30 are fully expanded.

This configuration of the threads 55, 63 may also prevent overexpansion of the elongate members 30. Once the threads 55, 63 disengage, the proximal tube 50 may not be directed distally further, thereby preventing further distal movement of the proximal hub 22. Thus, the relative length and location of the external and internal threads 55, 63 may be selected to provide a desired size and/or shape for the elongate members 30 in the expanded configuration. Optionally, the distal tube 60 may include a stop, e.g., an end wall (not shown), that prevents further distal movement of the proximal tube 50 when the distal end 54 enters the unthreaded region. This may prevent the user from forcing the proximal tube 50 further distally, which may over-expand and/or damage the elongate members 30 and/or supports 40.

When it is desired to collapse the elongate members 30, the proximal tube 50 may be rotated in a second opposite direction, e.g., counterclockwise. The external threads 55 may reengage the internal threads 63, and then thread the external threads 55 proximally, thereby directing the proximal hub 22 proximally. As the proximal hub 22 is directed proximally, the elongate members 30 and supports 40 may be pulled back radially inwardly towards the collapsed configuration, as shown in FIG. 3 If the stop 53 on the proximal tube 50 is not engaged with the proximal hub 22, e.g., is disposed proximal to the proximal hub 22, the proximal tube 50 may not pull the proximal hub 22 proximally. In this embodiment, the supports 40 and/or the elongate members 30 themselves may be sufficiently resiliently biased towards the collapsed configuration such that they push the proximal hub 22 proximally once the proximal hub 22 is no longer abutted by the stop 53.

Optionally, as best seen in FIGS. 3B and 4B, the proximal end 52 of the proximal tube 50 may also include a connector for engaging the expansion tool 70. For example, the proximal end 52 may include external threads, a hex head, and the like (not shown). With additional reference to FIGS. 1A and 1B, the expansion tool 70 may include an elongate body including a proximal end 72, a distal end 74, and a lumen 76 extending therebetween. A handle 78 may be provided on the proximal end 72, e.g., to facilitate manipulation and/or rotation of the expansion tool 70.

During use, the expansion tool 70 may be inserted between the elongate members 40 and engaged with the connector(s) on the proximal end 52 of the proximal tube 50 of the core member 20. Optionally, as shown in FIGS. 1A and 1B, the apparatus 10 may include a central tubular extension 21 that extends proximally from the core member 20 beyond the proximal ends 32 of the elongate members 30. In this embodiment, the tubular extension 21 may be inserted into the lumen 76 at the distal end 74 of the expansion tool 70, and then the expansion tool 70 may be advanced over the tubular extension 21.

The expansion tool 70 may be advanced until the distal end 74 engages with the proximal end 52 of the proximal tube 50 of the core member 20 (see FIG. 3). For example, the distal end 74 and the proximal end 52 may include mating threads, male-and-female keyed connectors, and the like. Thereafter, when the expansion tool 70 is rotated, the proximal tube 50 of the core member 20 may then also be rotated, and thereby translated axially as described elsewhere herein.

The apparatus 10 may be used for brachytherapy treatment within a tissue structure, for example within a breast (not shown). The breast may have a cavity (e.g., a lumpectomy cavity) formed therein by removal of cancerous tissue (also not shown). The apparatus 10 may be inserted in its collapsed position into the breast or other tissue structure. The apparatus 10 may be inserted via an existing incision (not shown), e.g., the incision used to perform the lumpectomy, or via a new incision created for delivering the apparatus 10.

During use, the apparatus 10 may be provided with the elongate members 30 in the collapsed configuration, as shown in FIGS. 1A and 3. The distal hub 24 may be inserted into a tract through tissue (either alone, e.g., using a sharpened or pointed distal tip, or via a cannula or other tubular member, not shown) until the elongate members 40 are disposed within a target tissue region, e.g., within a lumpectomy cavity. If the expansion tool 70 is separate from the apparatus 10, the expansion tool 70 may be connected to the apparatus 10.

The expansion tool 70 may then be rotated in a first direction to direct the proximal hub 2 distally relative to the distal hub 24, thereby causing the elongate members 30 to bow outwardly within the cavity, as shown in FIGS. 1B and 4. When the apparatus 10 is directed to the expanded configuration, the elongate members 30 may at least partially direct tissue surrounding the cavity outwardly and/or the tissue may invaginate between adjacent elongate members, as disclosed in the applications incorporated by reference above. Optionally, the elongate members 30 and/or the distal portion 14 may include one or more extensions, membranes, or other features to shape the cavity in a desired manner, also as disclosed in the applications incorporated by reference above.

Optionally, thereafter, the apparatus 10 may be secured relative to the target tissue region to prevent subsequent migration. Alternatively, the elongate members may sufficiently engage the surrounding tissue to prevent substantial migration. If the apparatus 10 is to remain within the target tissue region for an extended period of time, the expansion tool 70 may be removed from the apparatus 10.

One or more radiation sources (not shown) may then be directed into the lumens 36 of the elongate members 30 to deliver radiation to the tissue surrounding the cavity. Thus, the elongate members 30 may define pathways for receiving radiation source(s). If the core member 20 includes a lumen, one or more radiation sources may also be directed into the lumen of the core member 20. Alternatively, the elongate members 30 and/or core member 20 may include other features providing pathways extending between the proximal and distal portions 12, 14 of the apparatus 10. For example, the elongate members 30 may include grooves or tracks (not shown), which may receive one or more sources of radiation, as described in the applications incorporated by reference above.

In an exemplary procedure, a plurality of LDR sources may be delivered into the elongate members 30 and/or core member 20, and remain indwelling for a predetermined time. For example, individual seeds, pods of seeds, or other radiation sources may be loaded into respective elongate members 40 simultaneously or sequentially, thereby providing a three dimensional array of seeds or other radiation sources that may remain in the target location for an extended period of time. The seeds may be spaced apart on each pod or have different radioactive intensities, according to the dose plan. For example, the seeds in different portions of the array may also have different lengths and/or spacing along respective elongate members 10 such that the array is substantially asymmetrical, e.g., radially and/or axially relative to a central axis of the apparatus 10.

Alternatively, one or more HDR sources may be delivered sequentially or simultaneously into the elongate members 30 and/or core member 20 according to a desired dose plan, as described elsewhere herein. For example, an HDR source may be introduced into a first elongate member 30, advanced to a first position, and maintained at the first position for a predetermined time. The HDR source may then be advanced and/or retracted to a second position, and maintained there for a predetermined time, etc. The HDR source may then be removed from the first elongate member 30, and then introduced sequentially into each of the other elongate members 30 in a similar manner. In a further alternative, one or more radiation sources may be preloaded or secured within the elongate members 30 before introduction into the cavity. Additional information on use of the apparatus 10 may be found in the applications incorporated by reference above.

Upon completion of the brachytherapy treatment, the apparatus 10 may be returned to its collapsed configuration, and the apparatus 10 removed from the breast via the insertion incision. For example, if the expansion tool 70 has been removed, the expansion tool 70 may be introduced and reconnected to the proximal tube 50. The expansion tool 70 may then be rotated to rotate the proximal tube 50 of the core member 20 and collapse the elongate members 30 back to the collapsed configuration, as described elsewhere herein.

Before treating the patient, it may be desirable to create a dose plan to determine the course of treatment. Dose planning may be accomplished using a variety of imaging methods (e.g., CT or ultrasound) and/or using dose planning software for either HDR or LDR applications. The timing and general scenario of the dose planning process is at the discretion of the clinical physicist/oncologist. However, one such scenario may include placing the apparatus 10 into the target tissue region and actuating the distal portion 14 into the deployed configuration. Then, with the aid of imaging (e.g., CT), both the target tissue region and the position of the elongate members 30 may be delineated. A dose plan may then be developed and, if desired, modified as configuration adjustments are made to the apparatus 10 and/or the elongate members 30.

To assist with dose planning, it may be desirable to provide one or more marker devices, e.g., within the lumens of the elongate members 30. The marker devices may be provided from radiopaque or other materials that create an artifact or are otherwise detectable using the imaging device to identify the relative location and/or orientation of the elongate members 30.

Figure 6:
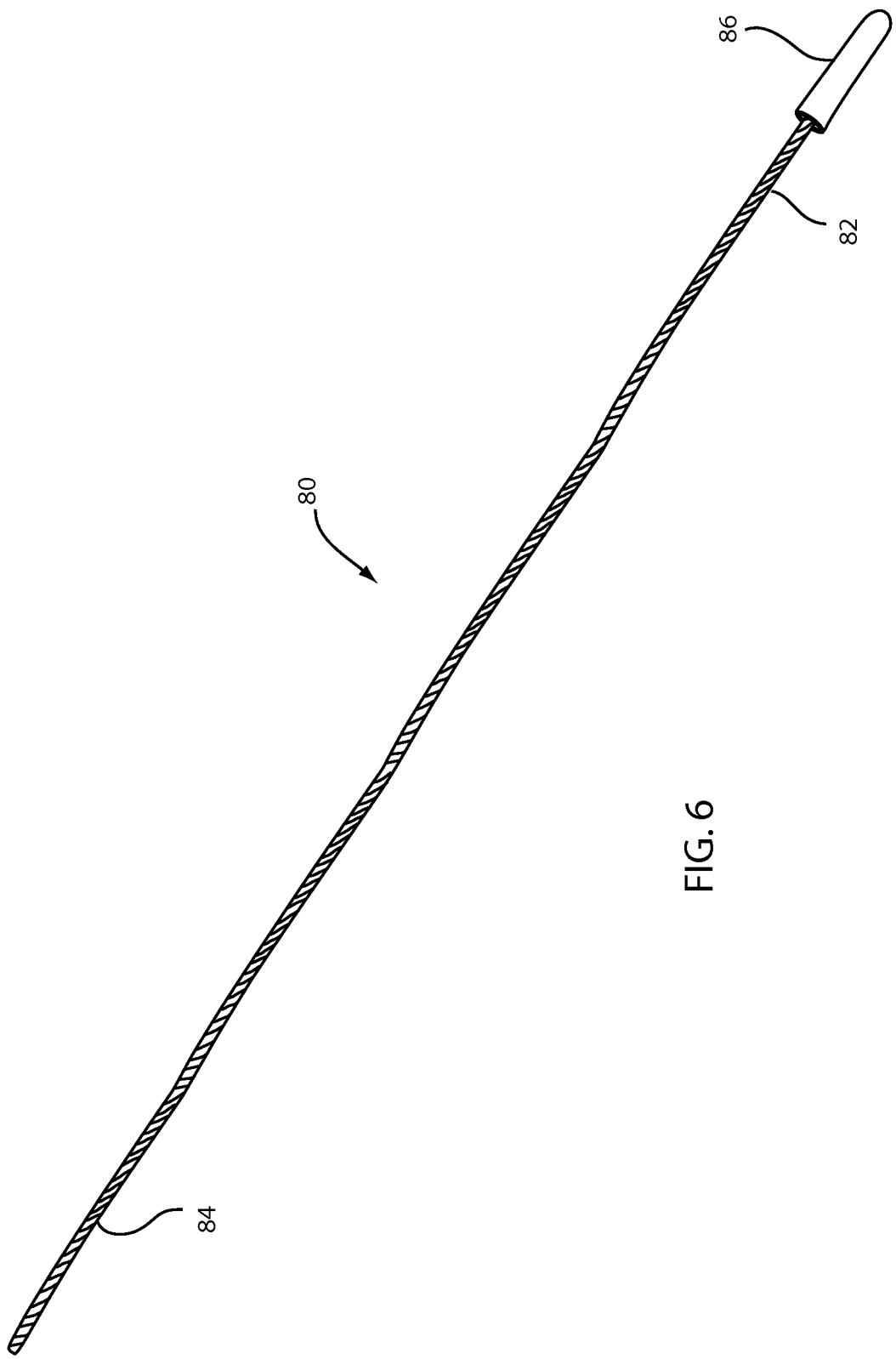
FIG. 6 is a side view of an end cap marker device that may be introduced into lumens of the apparatus, as shown in FIG. 2.

FIG. 6 shows an exemplary embodiment of a marker device 80 that may be provided. Generally, the marker device 80 includes an elongate body, e.g., a plastic-coated (e.g., nylon or FEP) stainless steel cable segment, including a proximal end 82 and a distal end 84. Optionally, the proximal end 82 may include an end cap 86 for sealing the lumen of an elongate member 30, as described further below.

The marker device 80 may have a length corresponding to the length of the elongate members 30, e.g., at least as long as the elongate members 30. For example, as shown in FIG. 2, the marker device 80 may be inserted into the lumen of an elongate member 30, e.g., until the distal end 84 of the marker device 80 is disposed within the distal end 34 of the elongate member 30, i.e., until the distal end 84 is disposed within or immediately adjacent to the distal hub 24. Similarly, a marker device (not shown) may be inserted into each of the other elongate members 30, e.g., until their distal ends are disposed within or immediately adjacent the distal hub 24.

Thereafter, the radiopacity of the marker devices 80 may enhance monitoring the location and/or orientation of the elongate members 30 by identifying the marker devices 80. For example, the marker devices 80 may delineate the entire path for an HDR catheter, e.g., using x-ray or other imaging modalities, such as CT. The distal ends 84 of the marker devices 80 may also be used to help identify an initial dwell position of an HDR source introduced sequentially into the elongate members 30 (after removing the marker devices 80). Optionally, one or more radiopaque markers, e.g., a gold or other band (not shown), may be provided on the distal end 84, e.g., by crimping, welding, bonding, and the like to enhance radiopacity of the distal end 84.

When the dose plan is optimized, the characteristics of the radioactive sources (e.g., brachytherapy devices) are chosen (e.g., LDR seed activity levels, HDR dwell positions and/or times, etc.), and prepared for placement into the apparatus 10 via the openings in the proximal ends 32 of the elongate members 30. The marker devices 80 may then be removed before treatment.

The marker devices 80 may also support the elongate members 30. For example, a cable may provide a relatively strong yet flexible support that may be inserted into the elongate members 30 between treatments. Thus, the marker devices 80 may prevent kinking or other deformation or damage to the elongate members 30 between treatments, e.g., for HDR therapies.

Optionally, the marker device 80 may be used to seal the lumen 36 of an elongate member 30, e.g., to prevent fluid, debris, and the like from entering. As shown, the marker device 80 may include an end cap 86 on the proximal end 82, which may be seated over or otherwise seal the proximal end 32 of an elongate member 30. For example, between treatments, a marker device 80 may be inserted into each of the elongate members 30 of the apparatus 10, e.g., as shown in FIG. 2, until the end cap 86 is received over the proximal end 32. The end cap 86 may prevent fluid or other debris from entering the elongate member 30, which may block or otherwise compromise subsequent treatment.

Figure 6A:
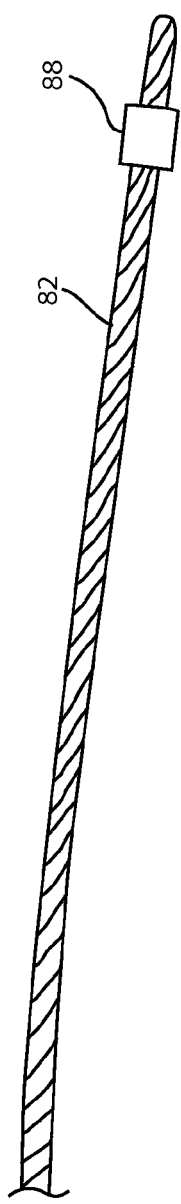
FIGS. 6A-6C are side views, showing stages of a method for making the end cap marker device of FIG. 6.
Figure 6B:
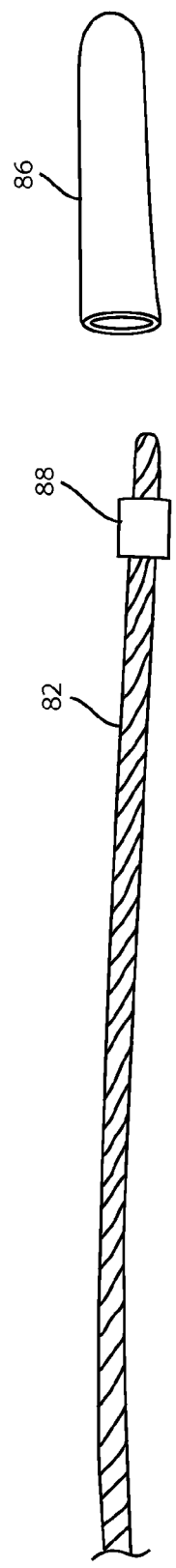
Figure 6C:
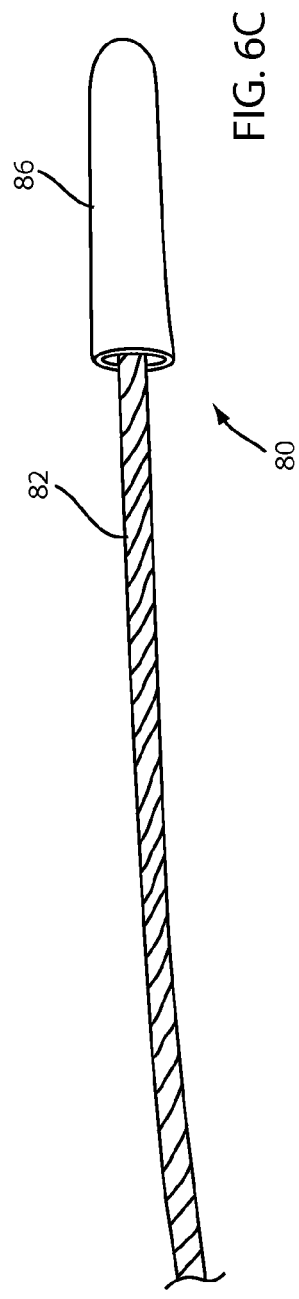

FIGS. 6A-6C show an exemplary method for making a marker device 80. Initially, a segment of cable may be provided, e.g., by cutting, extruding, and the like. A spacer 88 may be attached to the proximal end 82 of the marker device 80, e.g., by crimping a segment of stainless steel tubing or other bushing member onto the proximal end 82. Alternatively, the spacer 88 may be attached by interference fit, bonding with an adhesive, welding, and the like. The end cap 86, e.g., a plastic (such as vinyl) segment of tubing with an enclosed end, may then be slid over the spacer 88. The relative size of the spacer 88 and end cap 86 may be selected such that the end cap 86 is secured received over the spacer 88. Alternatively or in addition, the end cap 86 may be attached to the spacer 88, e.g., by bonding and the like.

The end cap 86 may extend distally beyond the spacer 88, thereby defining an annular pocket for receiving the proximal end 32 of an elongate member 30. The end cap 86 may be sized to frictionally engage the proximal end 32 received between the end cap 86 and the proximal end 82, thereby substantially sealing the lumen of the elongate member 30.

Figure 7:
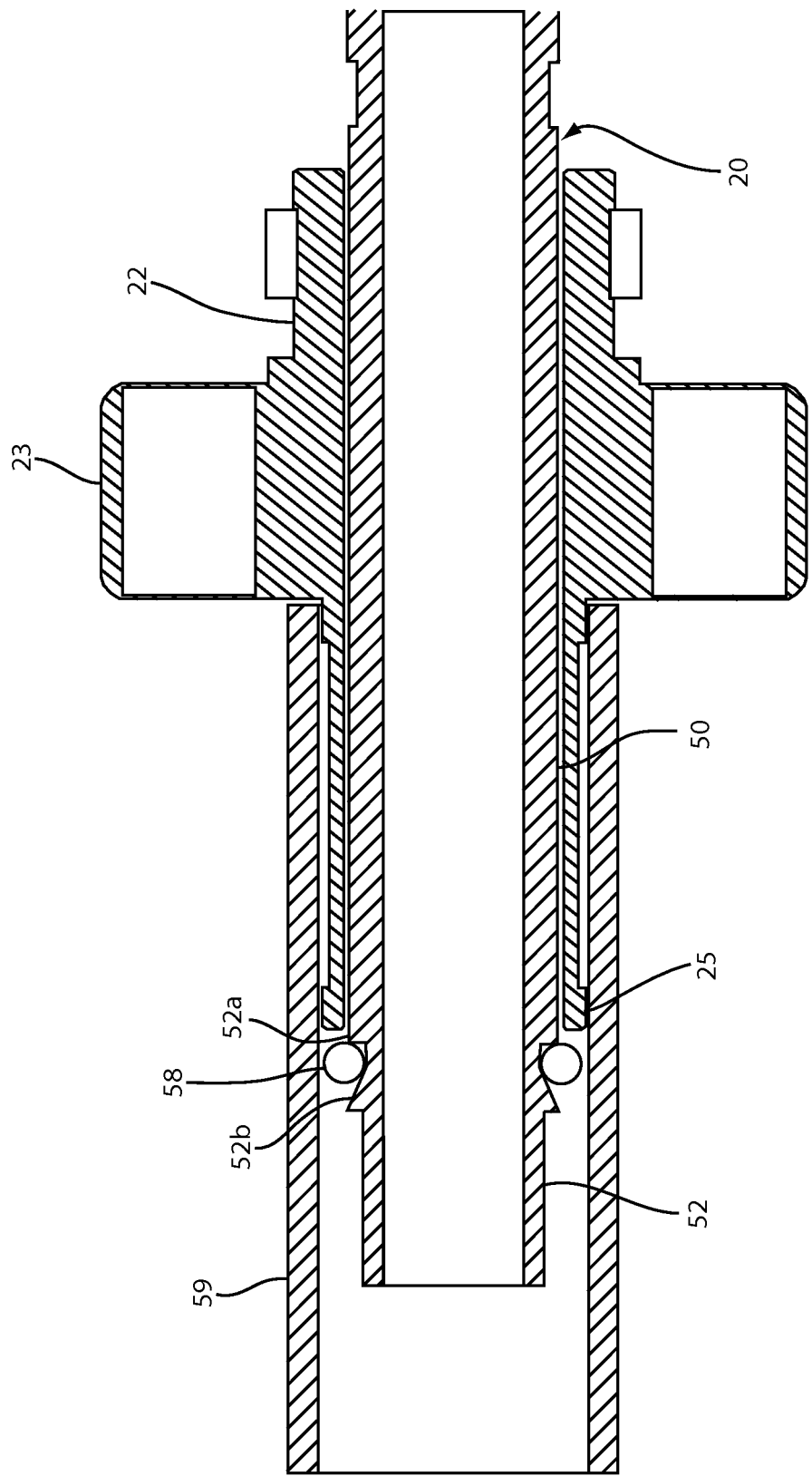
FIG. 7 is a longitudinal cross-section of an exemplary embodiment of a proximal hub that may be provided on an expandable brachytherapy apparatus to allow rapid collapse and/or removal of the apparatus.
Figure 8:
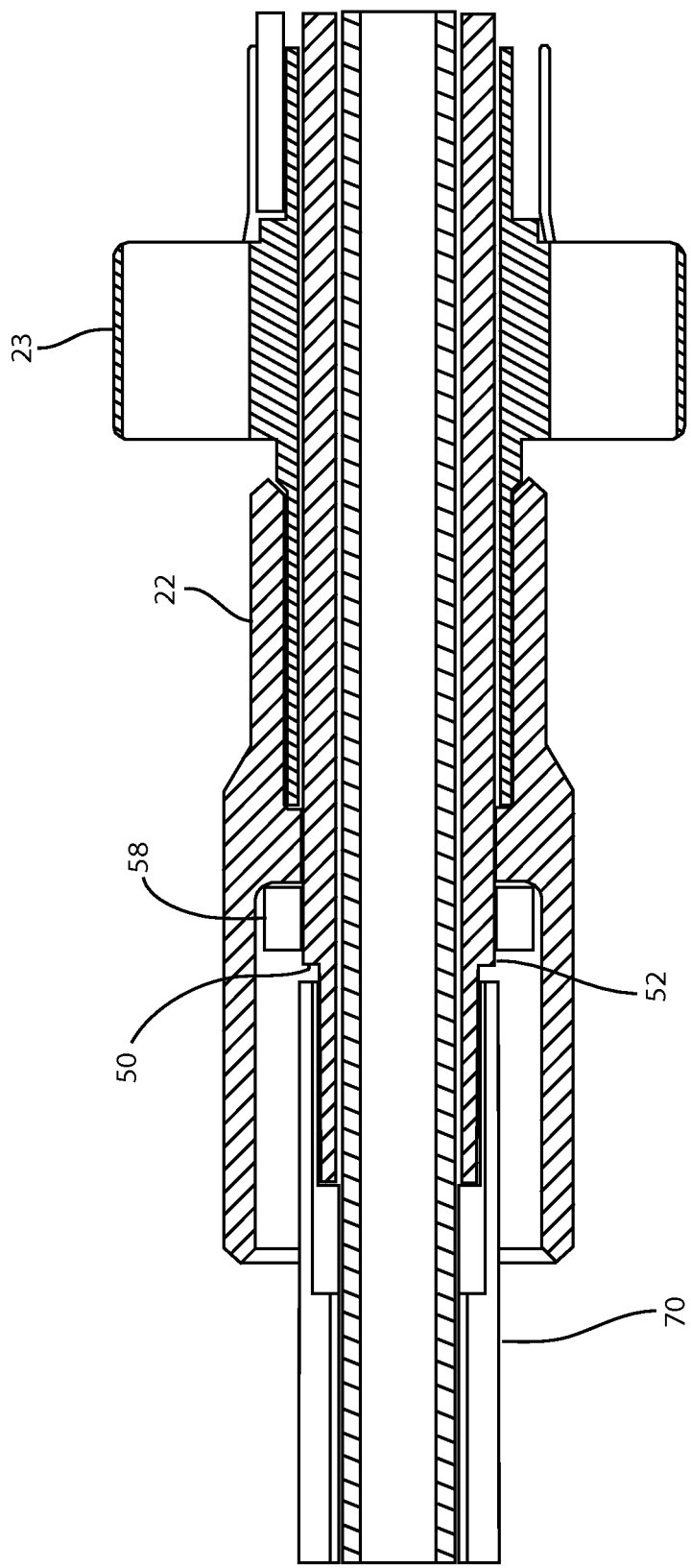
FIG. 8 is a longitudinal cross-section of another exemplary embodiment of a proximal hub that may be provided on an expandable brachytherapy apparatus to allow rapid collapse and/or removal of the apparatus.

Turning to FIGS. 7 and 8, exemplary embodiments of "bail-out" devices are shown that may be provided on the apparatus 10 or any of the embodiments disclosed in the applications incorporated by reference above. For example, with additional reference to FIGS. 3 and 4, it may be desirable to provide a mechanism to allow the proximal hub 22 to be disengaged from the core member 20, in particular the proximal tube 50 of the core member 20. Such disengagement may allow the elongate members 30 to be rapidly collapsed, e.g., to allow the apparatus 10 to be removed from a patient. Such rapid removal may be necessary, e.g., if an emergency arises that may be more easily acted upon if the apparatus 10 is removed more quickly rather than by reinserting the expansion tool 70 and collapsing the elongate members 30 normally. The bail-out configuration may also provide an additional safety feature if the apparatus 10 fails, e.g., if the proximal tube 50 cannot reengage the distal tube 60 of the core member 20 or if the mating threads 55, 63 somehow become locked or otherwise jammed.

For example, FIG. 7 shows a retaining ring 58 disposed around the proximal end 52 of the proximal tube 50 of the core member 20 adjacent to the proximal hub 22. The retaining ring 58 may be formed from an annular member, e.g., an enclosed o-ring, slotted ring, or "C" shaped ring. For example, the retaining ring 58 may be formed from a stainless steel or other substantially rigid ring that is cut to allow the ring to expand into a "C" shape when subjected to sufficient forces. As shown, the retaining ring 58 has a cross-section larger than an interior diameter of the proximal hub, e.g., at the proximal edge 25 of the proximal hub 22. This prevents the proximal hub 22 from being directed proximally relative to the proximal tube 50, since the retaining ring 58 cannot enter the passage through the proximal hub 22. The proximal end 52 of the proximal tube 50 includes a blunt edge 52a and a ramped edge 52b with the retaining ring 58 disposed between the edges 52a, 52b.

Thus, the retaining ring 58 may prevent axial movement of the proximal hub 22 and proximal tube 50 relative to one another. However, because of the ramped edge 52b, if sufficient axial force is applied, e.g., by pulling the proximal hub 22 relative to the proximal tube 50, the retaining ring 58 may elastically stretch and/or plastically deform allowing the retaining ring 58 to be directed up the ramped edge 52b. For example, the expansion tool 70 (not shown) may be coupled to the proximal tube 50, and the proximal hub 22 pulled proximally while preventing movement of the expansion tool 70. This may cause the proximal edge 25 to push the retaining ring 58 up the ramped edge 52b, thereby causing the retaining ring 58 to expand radially as it passes over the ramped edge 52b.

Once the retaining ring 58 passes beyond the ramped edge 52b, the retaining ring 58 may be released, thereby allowing the proximal hub 22 to be directed proximally relative to the proximal tube 50, thereby pulling the elongate members 30, e.g., towards the collapsed configuration. For example, the retaining ring 58 may be plastically deformed to a sufficiently large size that the retaining ring 58 no longer bears against the proximal tube 50. Alternatively, the retaining ring 58 may expand and break or otherwise yield as it passes over the ramped edge 52b. Thus, with a rapid, relatively high force (compared to normal use of the apparatus 10), the proximal hub 22 may be disengaged from the proximal tube 50 and allow rapid collapse of the elongate members 30.

Turning to FIG. 8, another embodiment of a retaining ring 58' is shown that is frictionally received around the proximal end 52 of the proximal tube 50 of the core member 20. Unlike the previous embodiment, the proximal end 52 of the proximal tube 50 does not include any raised ramps or edges to constrain the retaining ring 58.' Instead, the retaining ring 58' is maintained substantially stationary on the proximal tube 50 by friction, which may be overcome, e.g., by pulling the proximal hub 22 relative to the proximal tube 50 (and expansion tool 70, with sufficient force to cause the retaining ring 58' to slide proximally over the proximal tube 50. Thus, the proximal hub 22 may be pulled to collapse the elongate members 30 and allow rapid removal of the apparatus 10.

Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. For example, any of the treatment devices described herein may be combined with any of the delivery systems and methods also described herein. Thus, the invention is limited only by the following claims, and equivalents thereto.

We claim:

1. A brachytherapy treatment apparatus, comprising:
   an elongate body comprising a proximal end and a distal end configured for introduction into a tract through tissue to a target location within a patient's body;

a plurality of elongate members comprising a distal portion adjacent the distal end and a proximal portion configured to extend from the patient's body when the distal portion is introduced into the target location, the elongate members comprising lumens extending from openings in the proximal portion to the distal portion for receiving a source of radiation therealong, the distal portion of the elongate members being movable from a collapsed configuration for introduction through a tissue tract to a target location, and an expanded configuration; and a plurality of marker devices removably receivable into the openings and along the lumens of respective elongate members, each marker device comprising an elongate solid cable, wherein the marker devices are receivable within the lumens such that the marker devices extend through the lumens to the distal portion of the elongate members, and wherein the marker devices comprise end caps for engaging the openings in the elongate members when the marker devices are received within the lumens to substantially seal the lumens.

2. The apparatus of claim 1, wherein the marker devices comprise radiopaque material.

3. The apparatus of claim 1, wherein the marker devices have sufficient strength to support the elongate members.

4. The apparatus of claim 1, wherein the marker devices include distal ends that extend into the distal portion when the marker devices are fully received within the respective lumen, and wherein the marker devices include one or more markers on the distal ends thereof.

5. The apparatus of claim 4, wherein the markers are radiopaque markers to enhance radiopacity of the distal ends.

6. The apparatus of claim 1, wherein the marker devices provide relatively strong yet flexible support when received along the lumens of the elongate members to prevent kinking or other deformation or damage to the elongate members between treatments.

7. The apparatus of claim 1, further comprising an expansion tool adjacent the proximal portion and coupled to the elongate body for directing the elongate members between the collapsed configuration and the expanded configuration.

8. A brachytherapy treatment apparatus, comprising:
an elongate body comprising a proximal end and a distal end configured for introduction into a tract through tissue to a target location within a patient's body;
a plurality of tubular members comprising a distal portion carried by the elongate body and a proximal portion configured to extend from the patient's body when the distal portion is introduced into the target location, the tubular members comprising lumens extending between openings in the proximal portion to the distal portion for receiving a source of radiation therealong; and
a plurality of devices removably receivable into the openings and along the lumens of respective tubular members, each device comprising an end cap for engaging the opening of the respective tubular member when the device is received within the lumen of the tubular member to substantially seal the lumen.

9. The apparatus of claim 8, wherein the devices comprise radiopaque material.

10. The apparatus of claim 8, wherein the devices are receivable within the lumens such that the devices extend through the lumens to the distal portion.

11. The apparatus of claim 8, wherein the devices have sufficient strength to support the tubular members.

12. The apparatus of claim 8, wherein the devices provide relatively strong yet flexible support when inserted into the tubular members to prevent kinking or other deformation or damage to the tubular members between treatments.

13. The apparatus of claim 8, wherein the distal portion is movable from a collapsed configuration for introduction through a tissue tract to a target location, and an expanded configuration.

14. The apparatus of claim 8, wherein the devices include one or more markers on distal ends thereof.

15. The apparatus of claim 14, wherein the markers are radiopaque markers to enhance radiopacity of the distal ends.

16. A brachytherapy treatment apparatus, comprising:
an elongate core member comprising a proximal end and a distal end configured for introduction into a tract through tissue to a target location, the proximal and distal ends defining a longitudinal axis;
a distal hub coupled to the distal end of the core member;
a proximal hub on the proximal end of the core member and movable axially relative to the distal hub;
a plurality of tubular members coupled to the proximal and distal hubs and comprising a distal portion extending between the proximal and distal ends of the core member and a proximal portion extending proximally from the proximal hub and configured to extend from the patient's body when the distal portion is introduced into the target location, the distal portion of the tubular members movable from a collapsed configuration extending substantially parallel to the longitudinal axis for introduction through a tissue tract to a target location, and an expanded configuration when the proximal hub is directed distally relative to the distal hub, the tubular members comprising lumens extending from openings in the proximal portion to the distal portion for receiving a source of radiation therealong; and
a plurality of devices removably receivable along the lumens of respective tubular members, each device comprising an elongate body including a distal end sized for introduced into the opening and lumen of a respective tubular member, and an end cap on a proximal end of the elongate body that is receivable over the proximal end of the respective tubular member when the device is received within the lumen of the tubular member to substantially seal the lumen.

17. The apparatus of claim 16, wherein the devices include one or more markers on the distal ends thereof.

18. The apparatus of claim 16, wherein the devices comprise radiopaque material.

19. The apparatus of claim 18, wherein the devices comprise radiopaque markers to enhance radiopacity of distal ends of the tubular members.

20. The apparatus of claim 16, wherein the devices are receivable within the lumens such that the devices extend through the lumens to the distal portion of the tubular members.

21. The apparatus of claim 16, wherein the devices have sufficient strength to support the tubular members.

22. The apparatus of claim 16, wherein the devices provide relatively strong yet flexible support when inserted into the tubular members to prevent kinking or other deformation or damage to the tubular members between treatments.

23. The apparatus of claim 16, further comprising an expansion tool adjacent the proximal portion and coupled to the core member for moving the proximal hub axially relative to the distal hub to direct the elongate members between the collapsed configuration and the expanded configuration.

24. A brachytherapy treatment apparatus, comprising:
- an elongate body comprising a lumen extending from an opening in a proximal end of the elongate body to a closed distal end of the elongate body for receiving a source of radiation therein, the elongate body sized for introduction into a tract through tissue to a target location within a patient's body;
- a plurality of tubular members comprising a distal portion adjacent the distal end of the elongate body and a proximal portion configured to extend from the patient's body when the distal portion is introduced into the target location, the distal portion of the tubular members movable from a collapsed configuration for introduction through a tissue tract to a target location, and an expanded configuration for contacting surrounding tissue at the target location, the tubular members comprising lumens extending from openings in the proximal portion to closed ends in the distal portion for receiving a source of radiation; and
- a plurality of devices removably receivable into the openings and along the lumens of respective tubular members and the lumen of the elongate body, each device comprising an end cap for engaging the opening of the respective tubular member when the device is received within the lumen of the tubular member to substantially seal the lumen.

25. The apparatus of claim 24, further comprising an expansion tool adjacent the proximal portion and coupled to the elongate body for directing the tubular members between the collapsed configuration and the expanded configuration.

* * * * *